(12) United States Patent
Shippert

(10) Patent No.: US 6,482,200 B2
(45) Date of Patent: Nov. 19, 2002

(54) CAUTERY APPARATUS AND METHOD

(76) Inventor: Ronald D. Shippert, 4975 S. Albion St., Littleton, CO (US) 80121

( * ) Notice: Subject to any disclaimer, the term of this patent is extended or adjusted under 35 U.S.C. 154(b) by 30 days.

(21) Appl. No.: 09/753,700

(22) Filed: Jan. 3, 2001

(65) Prior Publication Data

US 2002/0087154 A1 Jul. 4, 2002

(51) Int. Cl.$^7$ ............................................... A61B 18/10

(52) U.S. Cl. .......................... 606/30; 219/233; 219/240

(58) Field of Search ..................... 606/30; 607/151; 219/240, 233; 200/293.1

(56) References Cited

U.S. PATENT DOCUMENTS 4,359,052 A * 11/1982 Staub ........................... 606/30

* cited by examiner

Primary Examiner—Lee Cohen
(74) Attorney, Agent, or Firm—Sheridan Ross P.C.

(57) ABSTRACT

A battery operated, hand-held cautery apparatus including a cauterizing unit with a cautery body and a heating assembly having a heating element, a switch assembly, and a housing assembly is disclosed. The switch assembly is essentially the position of a battery. That is, the battery acts as a switch. Power is not supplied to the heating element when the battery is in a first position, but power is supplied to the heating element when the battery is moved to a second position. The housing assembly may include a biasing member in contact with the battery such that the biasing force of the biasing member must be overcome to move the battery from the first position to the second position and thus energize the heating element.

19 Claims, 5 Drawing Sheets

CAUTERY APPARATUS AND METHOD

FIELD OF THE INVENTION

The present invention relates to battery powered devices and more particularly to a battery powered cautery device where the battery operates as a switch to operate the device.

BACKGROUND OF THE INVENTION

It is well known in the medical field to use instruments for cauterizing tissue of a patient for such purposes as sealing ruptured blood vessels and closing wounds. Often, such cautery devices are battery operated, hand-held devices. The size and convenience of the cauteries has expanded their use to such tasks as removing stitches.

A typical battery operated, hand-held cautery device includes a heating element electrically connected to a power source (e.g., a battery), a switch for selectively supplying power from the battery to the heating element, and a housing for enclosing the battery and associated electrical connections. The housings for these devices are commonly cylindrical.

Although various battery operated, hand-held cauteries have been developed, some perceived disadvantages remain. Generally, present cauteries last too long for an average use or procedure. Thus, the surgeon must decide whether to keep the cautery for another patient procedure or discard it. The cauteries, however, are typically designed for one time use and cannot be sterilized. For example, the materials of manufacture of many of these cauteries melt if steam sterilized. In some cases, sterile covers are provided with, or sold separately for, the cautery. Unfortunately, true sterility is not obtained by the use of a sterile cover. Medical care may be compromised when reusing a cautery apparatus. Therefore, there is a need for a more economical cautery that may be used once and then disposed of.

Present cauteries are also expensive. The higher cost is due, in part, to the incorporation of an independent switch into the design of the cautery. The inclusion of the independent switch into the cautery design increases both material and labor costs. Material costs are increased because of the additional parts required, while labor costs are necessarily increased to assemble the switch. The expense of present cauteries compounds the difficulty, mentioned above, of the surgeon to decide whether to discard a used cautery or retain it for subsequent use.

The addition of a individual switch in the cautery design creates other perceived disadvantages. Occasionally, a cautery may be accidentally activated by contact with the switch since many switches have little resistance to actuation. Accidental energizing may cause physical harm to the patient or the surgeon.

One additional perceived problem with present cauteries is the cylindrical housing. The cylindrical housing may allow the cautery to roll off of the field of surgery. The cautery may be damaged if it falls to the floor. Additionally, if the cautery heating element is hot, the surgeon or patient may be harmed.

In view of these perceived deficiencies in cautery devices, it would be beneficial to provide a hand-held, battery-powered cautery device that is lower in cost. It would be especially advantageous to provide a cautery device that does not require an individual switch yet is capable of being selectively energized. Additionally, it would be beneficial to provide a cautery device in which significant resistance is required to energize the heating element such that accidental energizing does not occur. It would also be advantageous to provide a cautery device that is incapable of rolling from a surface on which it is placed.

SUMMARY OF THE INVENTION

The cautery apparatus of the present invention includes a cauterizing unit, a switch assembly, and a housing. The cauterizing unit includes a cautery body and a heating assembly with a heating element. The housing encloses at least part of the battery.

The switch assembly consists, or essentially consists, of a battery having a first position and a second position. When the battery is in the first position, the heating element is deactivated. When the battery is in the second position, power is supplied to the heating element to energize it. In this way, the battery itself may act as the power switch for the heating element. The heating element may be activated and deactivated without the necessity of a movable switch element.

The battery, when in its second position, may be parallel, or nearly parallel, to the longitudinal axis of the cautery body. When the battery is in its first position, the battery may form an angle with the longitudinal axis of the cautery body that is not parallel.

In another embodiment, the cautery apparatus may include a cauterizing unit, a battery subassembly, and a housing assembly. The cauterizing unit can include a cautery body and a heating subassembly including a heating unit. The housing assembly may surround at least portions of the battery subassembly. The battery subassembly may include at least one battery, the first battery. The battery subassembly alone provides a mechanism for selectively supplying power to the heating element.

The first battery can have a first position and a second position. As above, when the battery is in the first position, battery power is not supplied to the heating element. However, when the first battery is placed in its second position, battery power is supplied to the heating element When battery power is supplied to the heating element, the heating element may become hot. Further, the battery subassembly may include a second battery. The battery subassembly may enclose at least a portion of the second battery. The second battery may be parallel to the longitudinal axis of the cautery body. The first battery may be parallel to the second battery when the first battery is in its second position, but at an angle that is not parallel to the second battery when the first battery is in its first position.

The first battery has a power end and a ground end. When the first battery is moved from the first position to the second position, one of either the power end or the ground end remains substantially stationary while the other end moves.

The housing assembly may also include a battery housing with a biasing member in contact with the first battery. The biasing member provides a biasing force that must be overcome to move the first battery from the first position to the second position.

The cautery apparatus may also include a main housing surrounding the first battery. The main housing may include a film enclosure. The film enclosure may be film capable of shrinking when exposed to heat so as to minimize the surface area of the film enclosure. A non-conductive member may also be inserted between the movable end of the first battery and the corresponding electrical terminal contact to prevent electrical continuity between the battery and the terminal. The non-conductive member may be removed to allow the electrical continuity between these two points when desired, thus providing a safety feature to prevent unwanted activation of the heating element. The non-conductive member may be positioned through the film enclosure such that the non-conductive member may be removed without removal of the film enclosure.

In operation, activation/deactivation of the cautery apparatus is accomplished by providing a cauterizing unit of the present invention and moving a battery between a first position and a second position. The second position is at some angle relative to the first position. When in the second position, the battery closes the electrical circuit of the cautery apparatus and provides battery power to the heating element. The cautery apparatus may include a second battery. The second battery remains in its same position while the first battery is moved to activate the heating element. The first battery and second battery may be laterally adjacent to one another when the first battery is in the second position.

The cautery apparatus is deactivated by applying a releasing force to the first battery such that the first battery returns to the first position. The releasing force may be a force applied by the operator thereof to cause the first battery to move to the first position. Alternatively, the releasing force may be applied by a biasing member such that the operator only need to release the force applied to the first battery.

The step of supplying power to the heating element may be prevented by placing a non-conductive member in contact with the first member. The non-conductive member may be removed when prevention of supplying power in undesired.

DETAILED DESCRIPTION

Figure 1:
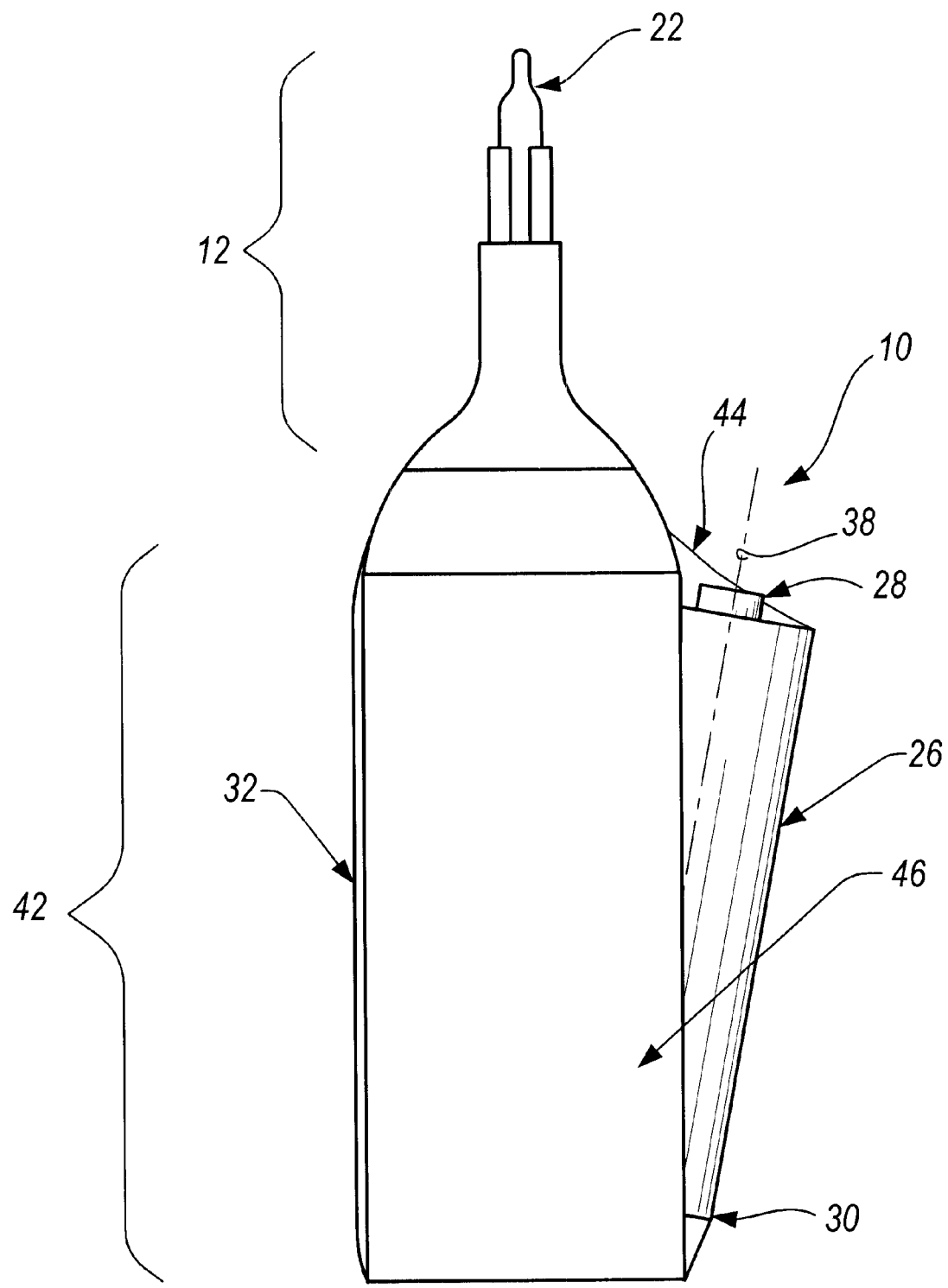
FIG. 1 is a side elevation view of one embodiment of the cautery apparatus of the present invention shown with the battery in the deactivated position.

With reference to FIG. 1, a cautery apparatus 10 with a cauterizing unit 12, a first battery 26, a second battery 32, and a housing assembly 42 is illustrated. The cauterizing unit 12 has a heating assembly 18. The heating assembly 18 includes a heating element 22 that is held to a cautery body 24. First battery 26 has first battery power end 28 and first battery ground end 30, and is shown in first battery first position 38. Housing assembly 42 includes battery housing subassembly 46 and film enclosure 44.

Figure 2:
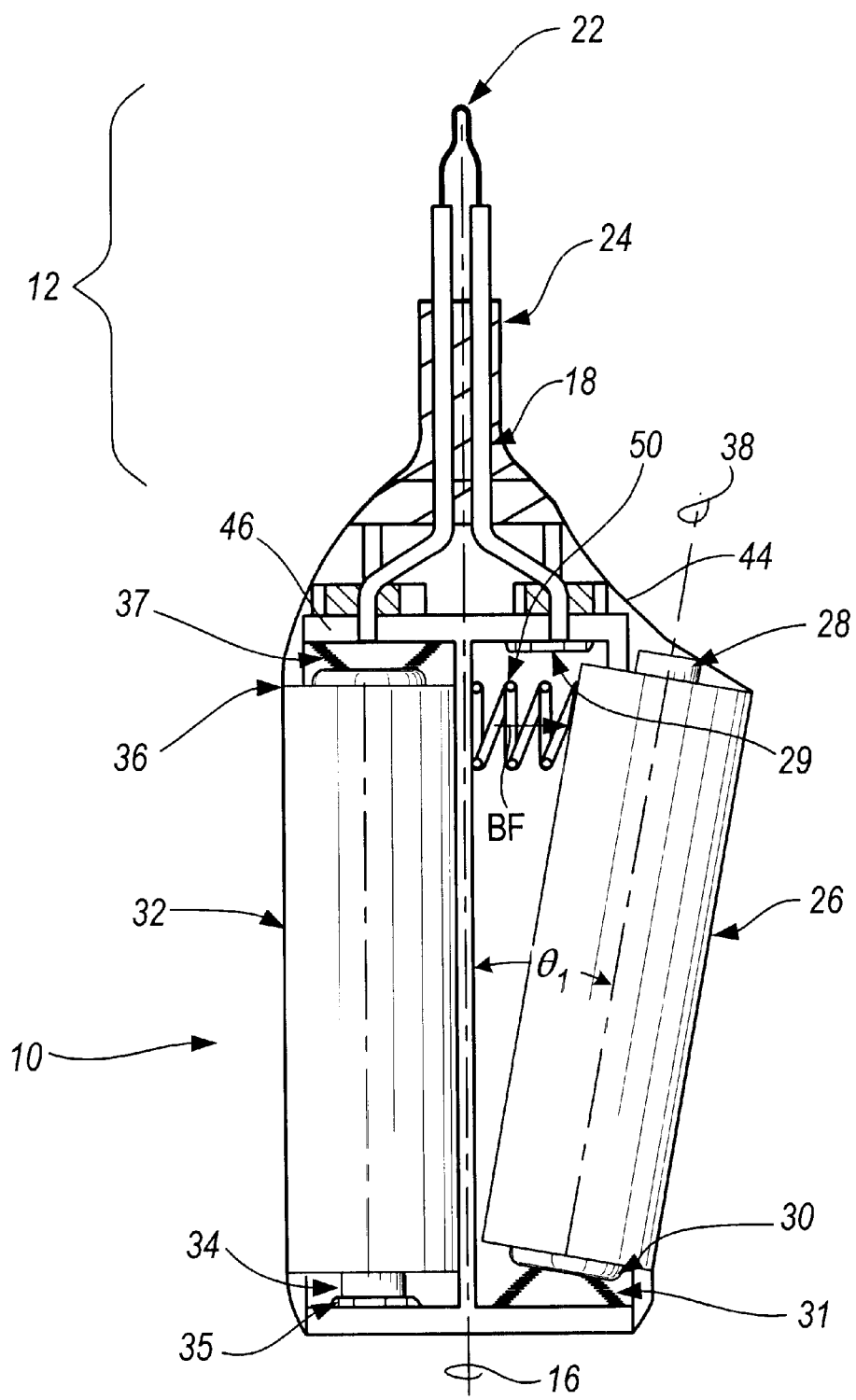
FIG. 2 is a cross-sectional view of the cautery apparatus of FIG. 1.

FIG. 2 shows the cautery apparatus 10 of FIG. 1 in cross-sectional view. Battery housing subassembly includes second battery 32. The battery housing subassembly 46 also includes battery terminal electrical connectors 29 and 31 for electrical contact with the first battery power end 28 and ground end 30, respectively. Similarly, the battery housing subassembly 46 includes battery terminal connectors 35 and 37, for electrical contact with the second battery power end 34 and ground end 36, respectively. First battery ground end electrical connector 30 and second battery power end electrical connector 35 are in electrical continuity with one another. First battery power end electrical connector 29 is in electrical contact with one end of the heating assembly 18, which in turn is in electrical contact with one end of the heating element 22. The opposite end of the heating element 22 is in electrical contact with the opposite end of the heating assembly 18, which is further electrically connected to second battery ground end electrical connector 37.

Battery subassembly 46 also includes biasing member 50 which is in contact with first battery 26. With the first battery 26 in first position 38, there is no electrical continuity between the first battery power end 28 and the first battery power end electrical connector 29. First battery 26 is maintained in first battery first position 38, in part, due to the biasing force BF exerted by biasing member 50. First battery first position 38 is related to the cautery body longitudinal axis 16 by first battery first position angle $\theta_1$. Film enclosure 44 also aids in maintaining first battery 26 in the first position 38 by preventing biasing member 50 from rotating first battery 26 beyond first position angle $\theta_1$.

Biasing member 50 is shown in FIG. 2 as a spring. It is understood, however, that other resilient devices capable of providing a biasing force would work equally well. For example, the biasing member 50 may include a polymer composition or a pre-formed flexible extension of battery housing subassembly 46 made of plastic.

Figure 3:
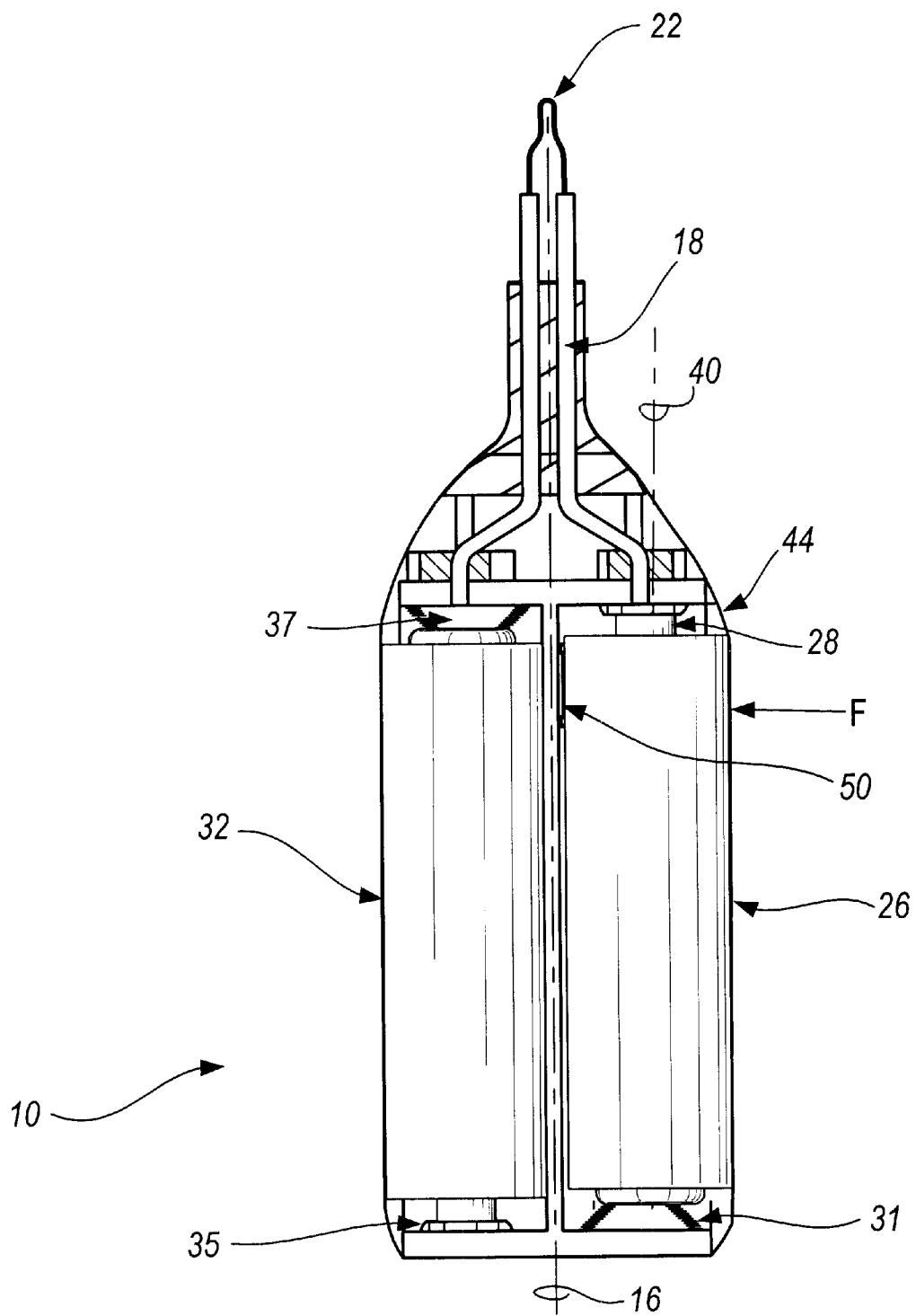
FIG. 3 is a cross-sectional view of the embodiment of the cautery apparatus of FIG. 1 with the battery in the activated position.

With reference to FIG. 3, the cautery apparatus 10, as described above, is shown with first battery 26 in second position 40. First battery second position 40 is such that the first battery 26 is at least about parallel with cautery body 24 longitudinal axis 16. Placing first battery 26 in second position 40 is accomplished by applying force F, sufficient to overcome biasing force BF, to first battery 26. The movement of first battery 26 is accomplished while second battery remains substantially stationary.

With first battery 26 in second position 40, electrical continuity is created between first battery power end 28 and electrical connector 29. This continuity closes the circuit formed by first battery 26, first battery power end electrical connector 29, heating assembly 18 including heating element 22, second battery ground end electrical connector 37, second battery 32, second battery power end electrical connector 35, and first battery ground end electrical connector 31. Therefore, first battery 26 acts as a switch for the circuit and activates heating element 22 by providing power to the heating element 22. The circuit may be opened, and thus heating element 22 may be deactivated, by removing force F which allows biasing force BF to replace first battery 26 to first position 38.

Figure 4:
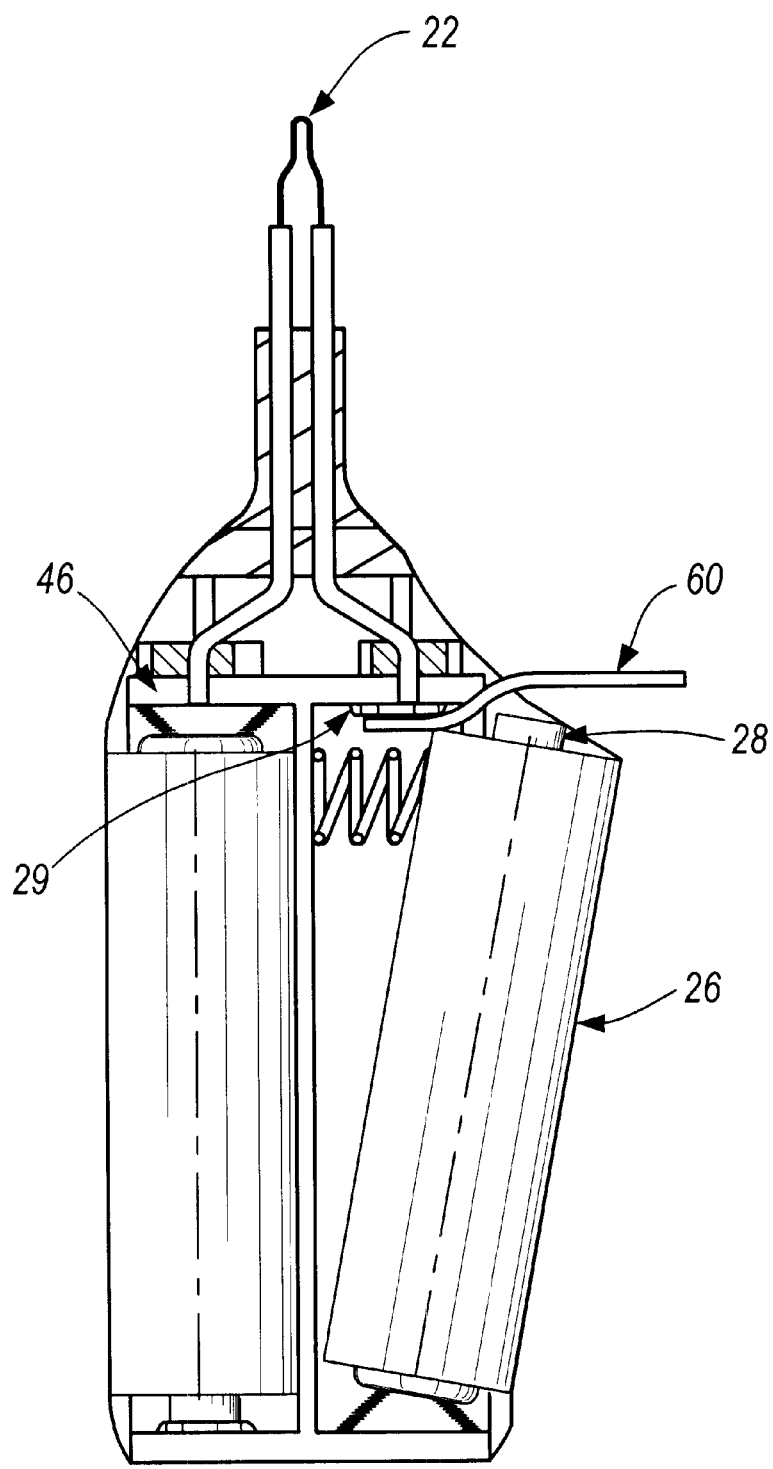
FIG. 4 is a cross-sectional view of an alternative embodiment of the cautery apparatus of the present invention.

FIG. 4 illustrates the cautery apparatus 10 as above with the optional feature of a non-conductive member 60. The non-conductive member 60 may be placed between first battery 26 and first battery power end electrical connector 29 to prevent electrical continuity between the first battery 26 and the electrical connector 29, regardless of the position of the first battery 26. Non-conductive member 60 may be removed to enable electrical continuity between first battery 26 and electrical connector 29 when desired. With this feature employed, non-conductive member 60 may act as a safety device to prevent unwanted activation of the heating element 22 by accidental contact with first battery 26.

The non-conductive member 60 is shown in FIG. 4 as a paper strip. It is understood, however, that other constructs of the non-conductive member 60 will work equally well. For example, the shape of non-conductive member 60 is limited only by size such that the non-conductive member 60 may be inserted into the battery housing subassembly 46 between first battery 26 and electrical connector 29. Further, any electrically insulating material may be used to construct non-conductive member 60 so long as the material characteristics withstand the applied forces without failing.

Figure 5:
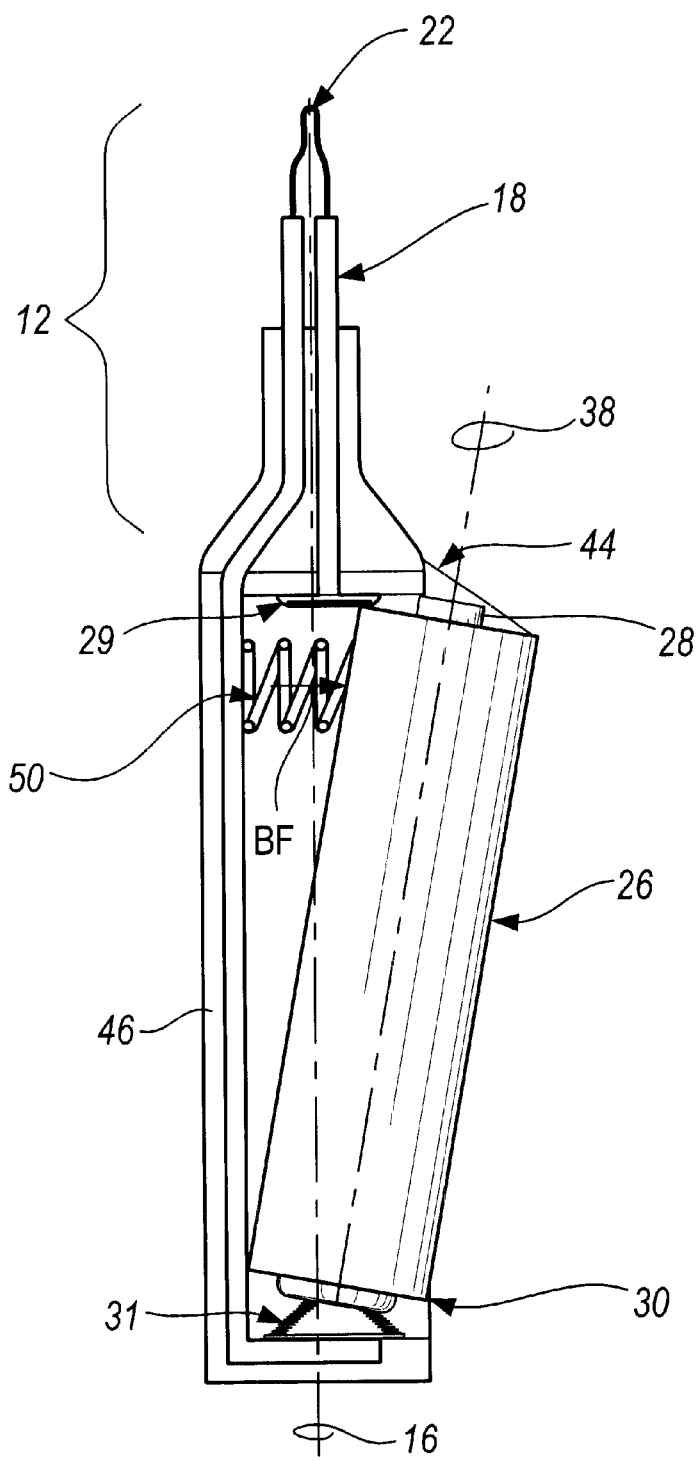
FIG. 5 is a side elevation view of another alternative embodiment of the cautery apparatus of the present invention.

With reference to FIG. 5, the cautery apparatus 10 of the present invention may also be designed to use only a single battery 26. The cautery apparatus 10 includes a cauterizing unit 12, a first battery 26, and a housing assembly 42 is illustrated. The cauterizing unit 12 has a heating element 22. First battery 26 has first battery power end 28 and first battery ground end 30, and is shown in first battery first position 38. Housing assembly 42 includes battery housing subassembly 46 with electrical connectors 29 and 31, a film enclosure 44, and a biasing member 50.

First battery 26 is maintained in first position 38 by biasing member 50 and film enclosure 44 at an angle $\theta_1$ relative to the cautery body longitudinal axis 16. In first position 38, first battery power end 28 is not in electrical continuity with first battery power end electrical connector 29, and thus the heating element 22 is deactivated. To activate the heating element 22, force is applied to first battery 26 to overcome biasing force BF of the biasing member 50 such that first battery 26 is in second position 40 (not shown). Removing the force applied to first battery 26 allows biasing force BF of biasing member 50 to replace first battery 26 in first position 38, and thus deactivates heating element 22.

When first battery 26 is in second position 40, the a circuit is formed between the following elements. First battery power end 28 is in electrical contact with electrical connector 29, which is, in turn, in electrical contact with one end of heating assembly 18. Heating element 22 is integral to, and electrically in series with, heating assembly 18. The opposite end of heating assembly 18 is in electrical contact with electrical connector 31, which is in electrical continuity with first battery ground end 30. First battery 26, by its position, acts as a switch to control activation and deactivation of the heating element 22.

The perceived problem of unwanted rolling of the cautery apparatus 10 even if the battery housing subassembly 46 is cylindrical. First battery 26, in first position 38, creates a non-spherical footprint which is incapable of roll.

In addition to being applicable to cauterizing instruments, the switch assembly of the present invention can be utilized in other devices or hardware in which it is desirable or suitable to eliminate a switch element and use a battery itself as the switch element. The uses can include for flashlights, penlights, personal grooming devices, powered hand tools (e.g., screwdrivers). Consequently, instead of a heating element being activated/controlled by a battery that also acts as a switch, other elements are activated such as light-producing, grooming, cutting, and fastening elements.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described herein are further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A cautery apparatus, comprising:

a cauterizing unit that includes a cautery body and a heating assembly having a heating element;

a switch assembly consisting essentially of a first battery having first battery power, said first battery having a first position and a second position wherein, when said first battery is in said first position, said first battery does not supply said first battery power to said heating element and, when said first battery is in said second position, said first battery supplies said first battery power to said heating element; and a housing assembly located about at least portions of said first battery.

2. An apparatus, as claimed in claim 1, wherein:

said first battery alone is used to cause a change between supplying and not supplying said first battery power to said heating element.

3. An apparatus, as claimed in claim 1, wherein:

said heating element is activated and caused to receive said first battery power from said first battery independently of any movable switch element.

4. An apparatus, as claimed in claim 1, further including:

a second battery electrically connected to said first battery when said first battery is in said second position.

5. An apparatus, as claimed in claim 1, wherein:

said cautery body has a longitudinal axis and when said first battery is in said first position, said first battery is at an angle different from parallel to said longitudinal axis.

6. An apparatus, as claimed in claim 1, wherein:

said housing assembly surrounds all of said first battery and portions of said cauterizing unit.

7. An apparatus, as claimed in claim 1, wherein:

said housing assembly includes a film enclosure surrounding said first battery.

8. An apparatus, as claimed in claim 1, wherein:

said housing assembly includes a battery housing subassembly and a main housing, with said main housing located about at least portions of said battery housing subassembly.

9. An apparatus, as claimed in claim 8, wherein:

said battery housing subassembly includes at least a first receptacle in which said first battery is located when said first battery is in said second position.

10. An apparatus, as claimed in claim 8, wherein:

said battery housing subassembly includes a biasing member in contact with said first battery and in which said biasing member has a biasing force that must be overcome to provide said first battery in said second position.

11. A cautery apparatus, comprising:

a cauterizing unit that includes a cautery body and a heating assembly having a heating element;

a battery subassembly including at least a first battery, wherein said battery subassembly alone controls supplying and not supplying battery power to said heating element, said first battery having a first position and a second position, when said first battery is in said first position, said battery power is not being supplied to said heating element and when said first battery is in said second position, said battery power is being supplied to said heating element, said battery subassembly including a second battery and when said first battery is in said first position, said first battery is located at an angle that is non-parallel relative to said second battery; and a housing assembly located about at least portions of said battery subassembly.

12. An apparatus, as claimed in claim 11, wherein:

said first battery has a power end and a ground end and, when said first battery is moved from said first position to said second position, one of said power end and said ground end moves while the other of said ground end and said power end remains substantially stationary.

13. An apparatus, as claimed in claim 11, wherein:

said housing assembly includes a battery housing having a biasing member that contacts said first battery.

14. An apparatus, as claimed in claim 11, wherein:

said housing assembly includes a main housing surrounding said first battery, with said main housing including a film enclosure.

15. A method for controlling activation/deactivation of a cautery apparatus, comprising:

providing a first battery and a cauterizing unit that includes a cautery body and a heating assembly having a heating element;

moving said first battery from a first position to a second position, said second position being at an angle relative to said first position; and supplying battery power to said heating element after moving from said first position to said second position.

16. A method, as claimed in claim 15, further including:

providing a second battery that remains in the same position during said moving step.

17. A method, as claimed in claim 16, wherein:

said first and second batteries are laterally adjacent to each other when said first battery is in said second position.

18. A method, as claimed in claim 15, further including:

removing said battery power to said heating element by releasing a force applied to said first battery.

19. A method, as claimed in claim 15, further including:

locating a non-conductive member in contact with said first battery to prevent said supplying step when said first battery is in said second position.

* * * * *